(12) United States Patent
Jensen

(10) Patent No.: US 9,480,627 B2
(45) Date of Patent: Nov. 1, 2016

(54) LONG TERM BACTERIOSTATIC COMPOUNDS AND THEIR USE IN RESTORATIVE DENTAL MATERIALS

(76) Inventor: Steven D. Jensen, South Jordan, UT (US)

( * ) Notice: Subject to any disclaimer, the term of this patent is extended or adjusted under 35 U.S.C. 154(b) by 0 days.

(21) Appl. No.: 13/257,647

(22) PCT Filed: Sep. 15, 2011

(86) PCT No.: PCT/US2011/051860
§ 371 (c)(1),
(2), (4) Date: Sep. 20, 2011

(87) PCT Pub. No.: WO2012/037424
PCT Pub. Date: Mar. 22, 2012

(65) Prior Publication Data
US 2013/0252207 A1  Sep. 26, 2013

Related U.S. Application Data

(60) Provisional application No. 61/383,163, filed on Sep. 15, 2010.

(51) Int. Cl.
*A61K 6/083* (2006.01)
*A61K 6/00* (2006.01)

(52) U.S. Cl.
CPC .......... *A61K 6/0835* (2013.01); *A61K 6/0067* (2013.01); *A61K 6/083* (2013.01)

(58) Field of Classification Search
CPC .................................................. A61K 6/0067
USPC ........................................................ 523/116
See application file for complete search history.

(56) References Cited

U.S. PATENT DOCUMENTS

| | | | | |
|---|---|---|---|---|
| 6,326,417 B1 * | 12/2001 | Jia | | 523/116 |
| 2003/0199600 A1 * | 10/2003 | Allred et al. | | 522/7 |
| 2003/0222366 A1 * | 12/2003 | Stangel et al. | | 264/16 |
| 2008/0233069 A1 * | 9/2008 | Tamareselvy et al. | | 424/70.11 |
| 2009/0093563 A1 * | 4/2009 | Qian | | 522/79 |
| 2012/0328682 A1 * | 12/2012 | Bardwell et al. | | 424/405 |

FOREIGN PATENT DOCUMENTS

GB   2461475 A   *   1/2010

\* cited by examiner

*Primary Examiner* — Michael Pepitone

(57) ABSTRACT

Example embodiments of the present invention utilize long term anti-microbial/bacteriostatic compounds that are dispersed throughout a tooth restoration material as a means to reduce or eliminate recurrent decay between the tooth restoration material and tooth structure. More specifically, the present invention utilizes metals, metal oxides, and metal salts, insoluble bacteriostatic organic compounds, soluble bacteriostatic organic compounds, and organometallic compounds as long term anti-microbial/bacteriostatic compounds that are dispersed throughout the tooth restoration material as a means to reduce or eliminate recurrent decay between the tooth restoration material and tooth structure.

3 Claims, No Drawings

LONG TERM BACTERIOSTATIC COMPOUNDS AND THEIR USE IN RESTORATIVE DENTAL MATERIALS

CROSS-REFERENCE TO RELATED APPLICATIONS

This application claims priority of PCT Application No. PCT/US 11/51860, filed Sep. 15, 2011, which is a non-provisional of U.S. Provisional Application No. 61/383,163, filed Sep. 15, 2010. Both applications are incorporated herein by reference in their entirety.

TECHNICAL FIELD OF THE INVENTION

The present invention relates to the field of dentistry and, more particularly, tooth restoration materials used in dentistry.

BACKGROUND OF THE INVENTION

Throughout the history of the dental profession, dental professionals have used a variety of tooth restoration materials in an attempt to effectively restore tooth structure, for example, for filling a cavity. One example of a now antiquated tooth restoration material is a compressed mercury-silver alloy known as an amalgam. Amalgam was once the more popular choice of tooth restoration materials due to the ability of the amalgam to provide a long term tooth restoration material solution.

Different from more modern tooth restoration materials, as will be discussed further below, a dental professional secures the amalgam into place without bonding the amalgam directly to the tooth substrate. Instead, amalgams are usually held in place within the tooth structure by compressing the amalgam into a mechanically retentive cavity formed within the tooth. For example, most amalgams require the dental professional to cut cavity preps to create mechanical undercuts within the tooth structure that physically hold the amalgam within the tooth cavity.

Due to the fact that amalgams do not actually bond directly to the tooth structure, oral fluids, microbes, foods and other substances found in the oral cavity are able to migrate or leak between the amalgam and the tooth structure. The migration of oral fluids, microbes, and food between the amalgam and the tooth structure would normally create an ideal situation for continued tooth decay, but amalgams contain silver and mercury, which continue to leach out from the amalgam, and in effect sterilize the cavity prep from further decay. The elemental and ionic forms of both silver and mercury can act as anti-microbial agents, and therefore, amalgams can control long-term tooth decay between the amalgam and tooth structure.

Although amalgams can control long-term tooth decay between the amalgam and the tooth structure, amalgams have a variety of disadvantages that have caused dental professionals to move away from the use of amalgams as a tooth restoration material. For example, one disadvantage of amalgams is that amalgams are not aesthetically pleasing because the opaque silver/black color of the amalgam contrasts greatly with the remaining white tooth. In general, patients generally feel that amalgam tooth restoration materials have a negative aesthetic appearance compared to the aesthetic appearance of the tooth before the amalgam is placed.

Another disadvantage of using amalgams is that in order for the dental professional to properly form the cavity preps, as generally described above, the dental professional is often required to remove an excessive amount of tooth structure than is preferred in order to correctly place an amalgam, including removing healthy tooth structure. In general, dental professionals always attempt to remove as little as healthy tooth structure as possible in order to maintain the integrity of the tooth, which can lead to a longer lasting tooth over the lifetime of a patient.

Despite the above and other disadvantages, dental professionals used amalgams for many years because suitable alternatives did not exist. More recently, however, additional tooth restoration materials were introduced in an attempt to overcome some of the disadvantages associated with amalgams. These additional tooth restoration materials may include primers, adhesives, cements, composites, and other direct or indirect materials. For example, more modern tooth restoration materials overcome the need for the dental professional to remove excessive tooth structure material, as required by amalgams, and allow for the use of tooth-colored filling materials.

As an overview, for example, the process of placing more modern tooth restoration materials includes the use of a tooth etching material, an adhesive, and a tooth-colored composite filling material. First, the tooth is etched with an acid to chemically remove the smear layer of dentin and surface-roughen the enamel of the cavity prep. Second, a low viscosity liquid adhesive is applied to the etched surface and allowed to penetrate into the tooth followed by polymerizing the adhesive into a solid polymer. Third, the remaining cavity is filled with a tooth-colored composite and polymerized/cured into a solid mass by means of various methods such as light curing with a light source. Since the modern tooth restoration materials bond directly to tooth structure, the dental professional does not need to remove excessive tooth structure. Moreover, the color of the modern tooth restoration materials can be controlled, providing an aesthetic advantage that causes the tooth restoration material color to closely match the color of the original tooth structure.

Notwithstanding the ability of the more modern tooth restoration materials to overcome the advantages of amalgams, the more modern tooth restoration materials also have various disadvantages. For example, many modern tooth restoration materials are made from organic compounds that may contain fairly inert non-toxic fillers (e.g., various powdered glasses). These tooth restoration materials are designed to be non-toxic, and are therefore unlike amalgams, are not sufficiently anti-microbial such that they can control decay between the restoration and tooth structure.

Furthermore, many modern tooth restoration materials require a polymerization process that will cause shrinkage of the filling material during the curing process. When these tooth restoration materials shrink, a gap between the tooth and restorative material may form that allows leakage to occur between the tooth structure and the tooth restoration materials. Due to the gap that forms, and the subsequent leakage, the tooth that was filled may begin to decay again because the more modern tooth restoration materials do not have anti-microbial properties.

In sum, metal amalgams are plagued with an unpleasant dark color, are made from toxic materials, and require excessive removal of tooth structure; yet, notwithstanding these deficiencies, do not suffer from recurrent decay after long-term tooth placement. On the other hand, more modern tooth restoration materials are tooth colored and non-toxic; yet, notwithstanding these advantages, suffer from recurrent decay after placement.

Accordingly, there are a number of disadvantages in the conventional art of tooth restoration materials.

SUMMARY OF THE INVENTION

Example embodiments of the present invention utilize long term anti-microbial/bacteriostatic compounds that are dispersed throughout a tooth restoration material as a means to reduce or eliminate recurrent decay between the tooth restoration material and tooth structure. More specifically, the present invention utilizes metals, metal oxides, and metal salts, insoluble bacteriostatic organic compounds, soluble bacteriostatic organic compounds, and organometallic compounds as long term anti-microbial/bacteriostatic compounds that are dispersed throughout the tooth restoration material as a means to reduce or eliminate recurrent decay between the tooth restoration material and tooth structure.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

DETAILED DESCRIPTION OF THE INVENTION

Example embodiments of the present invention utilize long term anti-microbial/bacteriostatic compounds that are dispersed throughout a tooth restoration material as a means to reduce or eliminate recurrent decay between the tooth restoration material and tooth structure. More specifically, the present invention utilizes metals, metal oxides, and metal salts, insoluble bacteriostatic organic compounds, soluble bacteriostatic organic compounds, and organometallic compounds as long term anti-microbial/bacteriostatic compounds that are dispersed throughout the tooth restoration material as a means to reduce or eliminate recurrent decay between the tooth restoration material and tooth structure.

Moreover, example embodiments of the present invention provide a tooth restoration material that not only includes antimicrobial/bacteriostatic properties, but is also aesthetically pleasing. In particular, example tooth restoration materials according taught by the present invention can be formulated to have a substantially tooth-colored appearance after placement. Therefore, example embodiments of the present invention provide a long term anti-microbial/bacteriostatic tooth restoration material that is also aesthetically pleasing to a patient after placement.

In addition to providing an aesthetically pleasing anti-microbial/bacteristatic tooth restoration material, example embodiments of the invention provide a tooth restoration material that is less toxic than amalgams. In addition, example embodiments of the tooth restoration materials, according to the present invention, provide direct bonding to the tooth structure. Direct bonding enables a dental professional to minimize the amount of tooth structure that must be removed in order to place the tooth restoration material.

Example embodiments of the tooth restoration material may be formulated to be various composites or compounds used in tooth restoration. For example, the tooth restoration material may be primers, bonding resins, etches, adhesives, filling materials or any other type of material that may be used in the tooth restoration process. The more preferred tooth restoration materials are those materials that remain in contact or directly proximate to the tooth structure after placement, however, tooth restoration materials according to the principles taught herein can be any material used to restore a tooth or a portion of tooth.

Depending on the type and purpose of the tooth restoration material, the tooth restoration material can be made from one or more of several components. For example, the tooth restoration material can include an anti-microbial/bacteriostatic compound, one or more monomers or polymers (including adhesive monomers), a photo initiator (including corresponding tertiary amine catalysts if applicable), a solvent, and/or a suspension aid. Various other components may also be included in the tooth restoration material in order to control various properties of the material, including viscosity, acidity, and other relevant properties to the tooth restoration material.

Examples of monomers that can be used in the tooth restoration material include, but are not limited to, Bisphenol A diglycidyl methacrylate, Diurethane dimethacrylate, triethylene glycol dimethacrylate, hydroxyl ethyl methacrylate, and any similar monomers with similar chemical and physical properties. The amount of monomers used in the tooth restoration material can depend on the particular monomer. For example, hydroxyl ethyl methacrylate can range from about 3% to about 8% of the total tooth restoration material. Other monomers can be used in the range of about 3% to about 75%, depending on the type and combination of monomers.

Examples of photo initiators include photo initiators that require a tertiary amine catalyst. For example camphorquinone, or similar photo initiator can be used in combination with ethyl-4-dimethylaminobenzoate as a tertiary amine catalyst. In addition, examples of photo initiators can include photo initiators that do not require a catalyst. In one example embodiment, Irgacure 2022 can be used as a photo initiator. The amount of photo initiator and/or photo initiator and catalyst combination can range from about 1% to about 3% of the total tooth restoration material.

Example solvents that can be included in the tooth restoration material can include solvents such as Ethanol or water. Other well known solvents in the dental industry can also be used. When used, the amount of solvents can range from about 20% to about 50% depending on the overall composition of the tooth restoration material.

The tooth restoration material can also include suspension aids. Example suspension aids can include, but are not limited to, silica powder and other similar and known suspension aids in the dental industry. The amount of suspension aids can range from about 7% to about 15% depending on the overall composition of the tooth restoration material.

Various example anti-microbial/bacteriostatic compounds that can also be included in the tooth restoration material. Example anti-microbial/bacteriostatic compounds include, but are not limited to, zinc oxide, insoluble copper compounds, zinc hydroxide, and zinc pyrithione and similar or equivalent compounds. These anti-microbial/bacteriostatic compounds are safe, non-toxic to humans, and substantially opaque white in nature, yet these anti-microbial/bacteriostatic compounds, when dispersed throughout the restorative material, can reduce or eliminate recurrent decay between the restoration material and tooth substrate. The amount of anti-microbial/bacteriostatic compounds can range from about 0.1% to about 4%.

Zinc oxide, zinc pyrithione and zinc hydroxide are very opaque and are used industrially to reduce visual transparency. Only a very small amount of zinc oxide, zinc pyrithione and zinc hydroxide are needed to modify a translucent composition into a completely opaque white composition. Teeth are not opaque white, so it is possible to make restorative materials too white, and therefore, lose their aesthetic appeal. Therefore, there is only a limited amount of zinc oxide, zinc pyrithione and/or zinc hydroxide that can be added to a tooth restoration material composition before it becomes too opaque and no longer desirable as a dental restorative material.

The preferred form of zinc oxide, zinc pyrithione and/or zinc hydroxide is in a finely divided state, such that the smaller the particle size the more advantageous the composition becomes. For example, it has been discovered that the smaller the particle size of the anti-microbial/bacteriostatic component, then the more surface area exposure at any given concentration in a composition. Therefore, the smaller the particle size, the increased ability to reduce the amount of zinc oxide, zinc pyrithione and/or zinc hydroxide in any given composition without significant efficacy loss to the anti-microbial/bacteriostatic properties due to dilution.

In addition, as the particles become sufficiently small, they begin to scatter less light and result in a more translucent tooth restoration material. By reducing the particle size of the zinc oxide, zinc pyrithione and/or zinc hydroxide compounds, the visual opacity can be reduced and the anti-microbial activity increased. An object of the present invention is thus to maximize the anti-microbial activity of zinc oxide, zinc pyrithione and/or zinc hydroxide while minimizing the visual opacity to result in a tooth restoration material that has effective anti-microbial properties as well as sufficient aesthetic properties.

It was discovered that an excellent balance between anti-microbial efficacy and aesthetic visual translucency is possible with zinc oxide, zinc pyrithione, and/or zinc hydroxide particles below about five (5) micron and even more translucent with compositions that contain about 100 nm particles. Notwithstanding, suitable tooth restoration materials can be manufactured when the anti-microbial/bacteriostatic compound has particles in the range of about 20 microns to about 100 nm or smaller. Generally speaking, the smaller the particles, the better the result.

As briefly mentioned above, some tooth restoration materials are more ideally suited for anti-microbial compounds than others, especially those tooth restoration materials that are in physical contact with the tooth surface. Tooth restoration materials that shrink during the polymerization process create a gap wherein leakage occurs. It is in this gap and at the margins that recurrent decay may occur. Therefore the tooth restoration materials that are placed adjacent the tooth structure are the best candidates for compositions that contain long-term anti-microbial compounds. Primers, bonding resins, adhesives, adhesive composites, flowable composites, paste composites and any other useful aesthetic material that is initially applied directly onto the tooth surface are ideal for the anti-microbial compounds of the present invention.

The present invention is much different than zinc poly cements Zinc poly cements are antiquated acid-base compositions that cure to a solid mass when mixed. They generally comprise zinc oxide powder that is mixed with aqueous poly acrylic acid such that an acid-base reaction occurs, with the final result being a solid zinc polyalkenoate salt. These early zinc poly cements were very weak (e.g., would break or not bond very well) and have been replaced.

The early zinc poly cements are similar to temporary zinc oxide/eugenol cements in that they are very opaque white and are not aesthetic. These types of cements were generally utilized in the posterior teeth or underneath prosthetics in order to make them less visible and noticeable. If placed on anterior teeth they would be very noticeable to the eye and therefore not aesthetically pleasing. Therefore, example embodiments of the present invention represent a step forward in technology compared to these early zinc poly cements.

Notwithstanding the various component and compounds that can be used, example embodiments of the present invention include the use of very small particles of anti-microbial/bacteriostatic compounds that are dispersed throughout polymerizable resins in such a manner and concentration that the finished restorative material is tooth-colored and aesthetically pleasing to the eye. In one example, the tooth restoration materials of the present invention can be used on anterior teeth, wherein the restoration can be closely matched in translucency and color to the remaining structure of a patients tooth.

Example embodiments of the present invention further include the use of aesthetic anti-microbial restorative materials for adhering, filling, and cementing permanent restorations utilizing polymerizable resin systems. Polymerizable resins as defined in this application do not include any restorative materials that harden by an acid-base reaction that result in a salt as the cured material. A polymerizable resin system for purposes of this application include a resin monomer or monomers with the appropriate catalysts and initiators such that polymerization can be controlled (e.g., light curable systems or chemical curable systems).

In practice, the small particle anti-microbial/bacteriostatic compounds are simply blended with one or more of the above described components until a finely dispersed suspension is formed. The following examples are illustrative of various example embodiments of a tooth restoration material according to the present invention; however, the invention is not confined to just these following examples. The various components are listed by % weight of the total composition.

Example 1

Enamel Bonding Resin 1. 30%—Bis-phenol A diglycidyl methacrylate monomer.
2. 40%—Diurethane dimethacrylate monomer
3. 1%—camphorquinone
4. 1%—ethyl-4-dimethylaminobenzoate
5. 0.3%—Zinc Oxide <100 nm powder
6. 27.7%—triethylene glycol dimethacrylate These materials were blended until thoroughly dispersed, forming a semi-translucent composition when light cured into thin layers.

Example 2

Enamel Bonding Resin 1. 30%—Bis-phenol A diglycidyl methacrylate monomer.
2. 40%—Diurethane dimethacrylate monomer
3. 1%—camphorquinone
4. 1%—ethyl-4-dimethylaminobenzoate
5. 0.1%—Zinc Oxide <5 micron powder
6. 27.9%—triethylene glycol dimethacrylate These materials were blended until thoroughly dispersed, forming a semi-translucent composition when cured into thin layers.

Example 3

Enamel Bonding Resin 1. 30%—Bis-phenol A diglycidyl methacrylate monomer.
2. 40%—Diurethane dimethacrylate monomer
3. 1%—camphorquinone
4. 1%—ethyl-4-dimethylaminobenzoate
5. 1.0%—Zinc Oxide <100 nm powder
6. 27%—triethylene glycol dimethacrylate These materials were blended until thoroughly dispersed, forming a more opaque composition than the previous compositions.

Example 4

Enamel Bonding Resin 1. 30%—Bis-phenol A diglycidyl methacrylate monomer.
2. 38.3%—Diurethane dimethacrylate monomer
3. 1%—camphorquinone
4. 1%—ethyl-4-dimethylaminobenzoate
5. 2.0%—Zinc pyrithione <100 nm powder
6. 27.7%—triethylene glycol dimethacrylate These materials were blended until thoroughly dispersed, forming a semi-translucent composition when cured into thin layers.

Example 5

Enamel Bonding Resin 1. 30%—Bis-phenol A diglycidyl methacrylate monomer.
2. 36.1%—Diurethane dimethacrylate monomer
3. 1%—camphorquinone
4. 1%—ethyl-4-dimethylaminobenzoate
5. 4%—Zinc pyrithione powder
6. 27.9%—triethylene glycol dimethacrylate These materials were blended until thoroughly dispersed, forming a semi-translucent composition when cured into thin layers.

Example 6

Enamel Bonding Resin 1. 30%—Bis-phenol A diglycidyl methacrylate monomer.
2. 40%—Diurethane dimethacrylate monomer
3. 1%—camphorquinone
4. 1%—ethyl-4-dimethylaminobenzoate
5. 1.0%—Zinc pyrithione powder
6. 27%—triethylene glycol dimethacrylate These materials were blended until thoroughly dispersed, forming a more opaque composition than the previous compositions.

In addition to the above examples, experimentation has surprisingly shown that zinc pyrithione is the most compatible ant-microbial/bacteriostatic compound with acrylic based adhesive systems Zinc pyrithione is surprisingly stable with acrylic dental adhesives and does not cure at 37 C over a nine month storage period.

The following are example embodiments of a dental adhesive tooth restoration material, illustrating the various components by % weight of the total composition.

Example 7

Dental Adhesive 1. 30%—Ethanol
2. 5%—Hydroxy ethyl methacrylate
3. 50.9%—Carboxylic acid, acrylic copolymer
4. 0.1%—Methoxy ethyl hydroxy quinone
5. 10%—Silica Powder
6. 2%—Irgacure 2022
7. 2%—Zinc pyrithione Example 8

Dental Adhesive 1. 30%—Ethanol
2. 5%—Hydroxy ethyl methacrylate
3. 48.9%—Carboxylic acid, acrylic copolymer
4. 0.1%—Methoxy ethyl hydroxy quinone
5. 10%—Silica Powder
6. 2%—Irgacure 2022
7. 4%—Zinc pyrithione These ingredients were blended together until homogenous and were allowed to remain in a sealed container in a 37 C oven for nine months. At nine months, the composition was still a liquid slurry and capable of light cure polymerization. A bonding test utilizing the dental adhesive to a set of mixed samples of bovine resulted in an average shear strength of 28.8 Mpa. These results are acceptable for a dentin/enamel adhesive for use a dental restoration material.

The present invention may be embodied in other specific forms without departing from its spirit or essential characteristics. The described implementations are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A tooth restoration material composition, comprising:
a polymerizable resin system that is light curable; and
an anti-microbial/bacteriostatic compound in the form of zinc pyrithione particles having an average size of less than five micron;
methoxy ethyl hydroxyl quinone; and
wherein the cured composition results in a tooth-colored material; and
wherein:
the zinc pyrithione comprises 2% of the composition by weight;
hydroxyl ethyl methacrylate comprises 5% of the composition by weight;
a copolymer comprises 50.9% of the composition by weight;
a photo initiator comprises 2% of the composition by weight;
ethanol comprises 30% of the composition by weight; and
silica powder comprises 10% of the composition by weight.

2. The tooth restoration material of claim 1, wherein the zinc pyrithione is in the form of particles having an average size of less than 200 nanometers.

3. The tooth restoration material of claim 1, wherein the zinc pyrithione is in the form of particles having an average size of less than 100 nanometers.

\* \* \* \* \*